United States Patent [19]
Siddiqui

[11] Patent Number: 6,146,664
[45] Date of Patent: Nov. 14, 2000

[54] STABLE TOPICAL ASCORBIC ACID COMPOSITIONS

[75] Inventor: Mukhtar Siddiqui, San Ramon, Calif.

[73] Assignee: Shaklee Corporation, Pleasonton, Calif.

[21] Appl. No.: 09/113,535

[22] Filed: Jul. 10, 1998

[51] Int. Cl.[7] ........................................ A61K 9/14
[52] U.S. Cl. ...................... 424/489; 424/70.12; 424/40 L
[58] Field of Search ..................................... 424/489, 401, 424/59, 47, 46, 470

[56] References Cited

U.S. PATENT DOCUMENTS

| | | |
|---|---|---|
| Re. 33,845 | 3/1992 | Schreuder . |
| 2,400,171 | 5/1946 | Ruskin . |
| 2,442,461 | 6/1948 | Karrer . |
| 2,585,580 | 2/1952 | Oppit . |
| 4,209,449 | 6/1980 | Mayhew et al. . |
| 4,367,157 | 1/1983 | Sherman . |
| 4,372,874 | 2/1983 | Modrovich . |
| 4,380,503 | 4/1983 | Koerner et al. . |
| 4,454,112 | 6/1984 | Tuominen . |
| 4,503,002 | 3/1985 | Mayhew et al. . |
| 4,563,346 | 1/1986 | Deckner . |
| 4,603,046 | 7/1986 | Georgalas et al. . |
| 4,698,178 | 10/1987 | Hüttinger et al. . |
| 4,784,845 | 11/1988 | Desai et al. . |
| 4,826,691 | 5/1989 | Prochnow . |
| 4,833,259 | 5/1989 | Erlemann et al. . |
| 4,847,267 | 7/1989 | Deckner et al. . |
| 4,904,698 | 2/1990 | Adkins, Jr. et al. . |
| 4,938,960 | 7/1990 | Ismail . |
| 4,940,574 | 7/1990 | Kaplan . |
| 5,008,100 | 4/1991 | Zecchino et al. . |
| 5,140,043 | 8/1992 | Darr et al. . |
| 5,141,665 | 8/1992 | Sherman . |
| 5,153,230 | 10/1992 | Jaffery . |
| 5,162,378 | 11/1992 | Guthauser . |
| 5,215,976 | 6/1993 | Fost et al. . |
| 5,286,719 | 2/1994 | Fost et al. . |
| 5,290,481 | 3/1994 | Todd, Jr. . |
| 5,290,555 | 3/1994 | Guthauser et al. . |
| 5,296,249 | 3/1994 | Todd, Jr. . |
| 5,308,621 | 5/1994 | Taylor et al. . |
| 5,372,805 | 12/1994 | Finkel et al. . |
| 5,374,362 | 12/1994 | McFarland . |
| 5,378,461 | 1/1995 | Neigut . |
| 5,384,115 | 1/1995 | Bissett et al. . |
| 5,391,321 | 2/1995 | Grüning et al. . |
| 5,445,823 | 8/1995 | Hall et al. . |
| 5,447,715 | 9/1995 | Roberts . |
| 5,482,705 | 1/1996 | Hoffmann, Jr. et al. . |
| 5,482,714 | 1/1996 | Jones et al. . |
| 5,505,935 | 4/1996 | Guerrero et al. . |
| 5,516,506 | 5/1996 | Fogel . |
| 5,543,135 | 8/1996 | Dahms . |
| 5,543,136 | 8/1996 | Aldous . |
| 5,560,917 | 10/1996 | Cohen et al. . |
| 5,573,754 | 11/1996 | Kulkarni et al. . |
| 5,573,785 | 11/1996 | Murphy . |
| 5,587,149 | 12/1996 | Punto et al. . |
| 5,587,151 | 12/1996 | Richard et al. . |
| 5,599,533 | 2/1997 | Stepniewski et al. . |
| 5,601,806 | 2/1997 | Katsumata et al. . |
| 5,605,694 | 2/1997 | Nadaud et al. . |
| 5,607,921 | 3/1997 | Bernard et al. . |
| 5,663,205 | 9/1997 | Ogawa et al. . |
| 5,663,270 | 9/1997 | Richard et al. . |
| 5,670,160 | 9/1997 | Eggensperger . |
| 5,738,859 | 4/1998 | Posner . |
| 5,746,945 | 5/1998 | Ryklin et al. . |
| 5,759,523 | 6/1998 | Hughes et al. . |
| 5,804,168 | 9/1998 | Murad . |
| 5,902,591 | 5/1999 | Herstein ................................... 424/401 |

FOREIGN PATENT DOCUMENTS

| | | |
|---|---|---|
| 0551030 | 9/1993 | U.S.S.R. . |
| WO 96/00060 | 1/1996 | WIPO . |

OTHER PUBLICATIONS

Alberts et al., Disposition and Metabolism of Topically Administered α–Tocopherol Acetate: A Common Ingredient of Commercially Available Sunscreens and Cosmetics, *Nutrition and Cancer* 26: 193–201 (1996).

Darr et al., Topical Vitamin C Protects Porcine Skin From Ultraviolet Radiation–Induced Damage, *British Journal of Dermatology* 127:247–253 (1992).

DeRitter et al., Effect of Silica Gel on Stability and Biological Availability of Ascorbic Acid, *Journal of Pharmaceutical Sciences* 59:229–233 (1970).

Gensler et al., Importance of the Form of Topical Vitamin E for the Prevention of Photocarcinogenesis, *Nutrition and Cancer* 26:183–191 (1996).

Harry, R.G., "Preservatives and Antioxidants," in *Harry's Cosmeticology: The Principles and Practice of Modern Cosmetics*, Chapter 41:655–690 (Ed: Harry) Leonard Hill Books, London (1973).

Idson, B., Vitamins and the Skin, *Cosmetics & Toiletries* 108:79–94 (1993).

Larrosa et al., Antiproliferative Effect of Intravitreal α–Tocopherol and α–Tocopherol–Acid–Succinate in a Rabbit Model of PVR, *Current Eye Research* 1030–1035 (1987).

Manowitz, M. and Sharpell, F., "Preservation of Cosmetics," *Disinfection, Sterilization, and Preservation*, Chapter 39:768–787 (Ed: Block) Lea & Febiger, Philadelphia (1977).

(List continued on next page.)

*Primary Examiner*—Thurman K. Page
*Assistant Examiner*—William E. Benston, Jr.
*Attorney, Agent, or Firm*—Klarquist Sparkman Campbell Leigh & Whinston, LLP

[57] ABSTRACT

An ascorbic acid (Vitamin C) composition in a nonaqueous or substantially anhydrous silicone vehicle has superior stability. Particulate ascorbic acid is substantially insoluble in the disclosed polyorganosiloxane vehicles, and the vehicle substantially excludes environmental oxygen. The ascorbic acid particles have surprisingly been found to have a high degree of bioavailability and effectiveness, for example in topical applications to reduce wrinkles and increase collagen growth and elasticity.

24 Claims, No Drawings

OTHER PUBLICATIONS

Mayer et al., The Effects of Vitamin E on the Skin, *Cosmetics & Toiletries* 108:99–109 (1993).

Mona Industries, Inc. (Paterson, NJ), Phospholipid CDM: Biomimetic Phospholipid Complex Product Description.

Palmieri et al., Vitamin E Added Silicone Gel Sheets for Treatment of Hypertrophic Scars and Keloids, *International Journal of Dermatology* 34:506–509 (1995).

Paton et al., Oats: Chemistry, Technology and Potential Uses in the Cosmetic Industry, *Cosmetics & Toiletries* 110:63–70 (1995).

Rieger, M.M., Oxidative Reactions in and on Skin: Mechanism and Prevention, *Cosmetics & Toiletries* 108:43–56 (1993).

Rigler, N.E. and Schimmel, J., "Preservation of Cosmetics," in Cosmetics: Science and Technology, Chapter 43: 1034–1074 (Ed: Sagarin) Interscience Publishers, Inc., New York (1957).

VERIS Research Summary, The Role of Antioxidants in Skin Care and Protection, *VERIS Research Information Service*, May 1997.

Alberts et al., Disposition and Metabolism of Topically Administered α–Tocopherol Acetate: A Common Ingredient of Commercially Available Sunscreens and Cosmetics, *Nutrition and Cancer* 26:193–201 (1996).

Darr et al., Topical Vitamin C Protects Porcine Skin From Ultraviolet Radiation–Induced Damage, *British Journal of Dermatology* 127:247–253 (1992).

Gensler et al., Importance of the Form of Topical Vitamin E for the Prevention of Photocarcinogenesis, *Nutrition and Cancer* 26:183–191 (1996).

Harry, R.G., "Preservatives and Antioxidants," in *Harry's Cosmeticology: The Principles and Practice of Modern Cosmetics*, Chapter 41:655–690 (Ed: Harry) Leonard Hill Books, London (1973).

Idson, B., Vitamins and the Skin, *Cosmetics & Toiletries* 108:79–94 (1993).

Manowitz, M. and Sharpell, F., "Preservation of Cosmetics," in *Disinfection, Sterilization, and Preservation*, Chapter 39:768–787 (Ed: Block) Lea & Febiger, Philadelphia (1977).

Mayer et al., The Effects of Vitamin E on the Skin, *Cosmetics & Toiletries* 108:99–109 (1993).

Mona Industries, Inc. (Paterson, NJ), Phospholipid CDM: Biomimetic Phospholipid Complex Product Description.

Paton et al., Oats: Chemistry, Technology and Potential Uses in the Cosmetic Industry, *Cosmetics & Toiletries* 110:63–70 (1995).

Rieger, M.M., Oxidative Reactions in and on Skin: Mechanism and Prevention, *Cosmetics & Toiletries* 108:43–56 (1993).

Rigler, N.E. and Schimmel, J., "Preservation of Cosmetics," in Cosmetics: Science and Technology, Chapter 43:1034–1074 (Ed: Sagarin) Interscience Publishers, Inc., New York (1957).

Tego Cosmetics, ABIL WE 09 Product Description.

VERIS Research Summary, The Role of Antioxidants in Skin Care and Protection, *VERIS Research Information Service*, May 1997.

6,146,664

STABLE TOPICAL ASCORBIC ACID COMPOSITIONS

FIELD OF THE INVENTION

This invention concerns a topical formulation of a bioavailable form of high levels of ascorbic acid (Vitamin C) that exhibits significant activity, but simultaneously is stable to oxidation from atmospheric oxygen, and is safe in use.

BACKGROUND OF THE INVENTION

Significant research has been performed over the past 60 years to develop formulations containing ascorbic acid (Vitamin C) that are stable to atmospheric oxidation. That research has been reported in numerous publications and patents, especially for formulations containing low concentrations of this important antioxidant. For example, Ciminera and Wilcox, "Stable Ascorbic Acid Solution for Parenteral Use" in *J. Am. Pharm. Assoc. Sci. Ed.* 35:363 (1946) discloses buffering aqueous ascorbic acid solutions with an alkaline sodium salt. Takashima, et al., "Ascorbic Acid Esters and Skin Pigmentation" in *Am. Perfumery and Cosmetics* 86:29 (July 1971) discloses the use of ascorbic acid esterified at the hydroxyl group of the third carbon with a phosphate group to yield a molecule that is stable in alkaline pH solutions.

U.S. Pat. No. 2,400,171 (Ruskin) discloses the conversion of ascorbic acid to its calcium or zinc salt to maintain stable aqueous solutions in the pH range of 7 to 7.3. U.S. Pat. No. 2,442,461 (Karrer) discloses stabilizing aqueous solutions of calcium ascorbate by adding an aliphatic thiocarboxylic acid, and maintaining the pH of the solution in the range of 5.2 to 5.6. U.S. Pat. No. 2,585,580 (Opplt) discloses the stabilization of ascorbic acid with thio-sugars, and maintaining the pH of the resulting solution in the range of 4.0 to 6.5. U.S. Pat. No. 4,367,157 (Sherman) discloses stabilizing aqueous ascorbic acid solutions in the pH range of 4 to 7 by adding monothioglycerol.

U.S. Pat. No. 4,372,874 (Modrovich) discloses adding a desiccant to a solution of ascorbic acid to entrap water and provide a residual water content below 0.5 weight percent, thereby forming a stable form of ascorbic acid. U.S. Pat. No. 5,140,043 (Darr et al.) discloses the stabilization of at least 1% (w/v) ascorbic acid by combining this material with equal parts water and a carrier comprising an alkylene glycol, and optionally a hydroxyalkylcellulose at a pH no greater than 3.5.

U.S. Pat. No. 5,296,249 (Todd) disclosed micron sized particles of ascorbic acid in a suspension medium in which the particles were insoluble. U.S. Pat. No. 5,308,621 (Taylor et al.) showed fine, particulate ascorbic acid suspended in a pharmaceutical carrier (such as a glycol or petroleum jelly) for transdermal systemic administration. U.S. Pat. No. 5,587,149 describes a polyethylene glycol-in-oil emulsion of ascorbic acid.

Ascorbic acid is biologically significant for many reasons, and has been found to have several different activities in the skin, as pointed out by Englard and Seifter, "The Biochemical Functions of Ascorbic Acid" in *Ann. Rev. Nutri.* 6:365 (1986). This vitamin has been found to be an antioxidant in blocking the lipid peroxidation of the skin, as demonstrated by Kunert and Tappel, "The Effect of Vitamin C on In-Vivo Lipid Peroxidation in Guinea Pigs as Measured by Pentane and Ethane Production" in *Lipids* 18:271 (1983). Furthermore, a significant amount of research has been published that describes the effects ascorbic acid has upon scavenging oxygen free radicals under a variety of normal and pathological conditions. Some of this research is included in the following partial list of texts on the subject.

1. *Oxidative Stress,* H. Sies, ed. (Academic Press, 1985)
2. *Free Radicals,* Aging and Degenerative Diseases, J. Johnson, Jr., R. Walford, D. Harmon and J. Miguel, eds. (Alan Liss, Inc., New York, 1986) 3. *Biological Role of Reactive Oxygen Species in Skin,* O. Hayaishi, S. Inamura and Y. Mayachi, eds. (Elsevier Press, New York, 1987) 4. *Free Radicals in Biology and Medicine,* B. Halliwell and J. Gutteridge, eds. (Clarendon Press, Oxford, 1985).

Additionally, ascorbic acid has been shown to stimulate collagen synthesis in-vitro, as detailed in the article entitled "Regulation of Collagen Biosynthesis by Ascorbic Acid: A Review" by S. Pinnell in *Yale J. Biol. Med.* 58:554 (1985).

As indicated by these references, although ascorbic acid is important to the skin, it is difficult to stabilize in topical preparations (such as dermatological, ophthamological or cosmetic formulations), particularly at the higher concentrations needed for maximum activity. The difficulties in preparing a stable topical preparation stem from the fact that ascorbic acid is an α-ketolactone having a double bond between the second and third carbon atoms of the structure, and hydroxyl groups at the second and third carbon atoms, and is therefore a moderately strong reducing agent. The pK of the molecule is 4.2, which means that one of the hydroxyl groups is 50% ionized at this pH value. At higher pH values the ascorbate anion becomes notoriously unstable. This instability is a result of several factors including sterochemical strain due to polar repulsion, the tendency of the molecule to disproportionate to dehydroascorbic acid (or dehydroascorbate anion) and ascorbic acid (or ascorbate anion) in the presence of a one-electron oxidant, or by a simple hydration reaction due to the attack of either a hydronium ion (or hydrogen ion) or a hydroxyl ion on the molecule, which opens the lactone ring structure.

There have been pharmaceutical (such as dermatological and ophthamological) and cosmetic products previously developed and marketed which contain esters of ascorbic acid in non-aqueous vehicles. However, none of these formulations contained high levels of the ascorbic acid ester that simultaneously demonstrated efficacy and stability. These non-aqueous formulations primarily used esters, fatty acids and fatty alcohols as the vehicles for delivery of the ascorbic acid ester.

SUMMARY OF THE INVENTION

For reasons that are not completely understood, solid, particulate ascorbic acid in a silicone-based, non-aqueous vehicle has been found to provide a stable formulation that delivers ascorbic acid to the skin in such a way that it is still active in performing its desired functions. The solid ascorbic acid is substantially completely insoluble in the silicone-based vehicle, and the vehicle provides an ideal reservoir for delivering the ascorbic acid into the skin where it is more soluble in the moisture-laden levels of the skin. Regardless of the reason for the effect, it has unexpectedly been found that the combination of the solid ascorbic acid dispersed in the silicone-based vehicle delivers the intended effect on the skin while simultaneously being safe and effective.

In particular embodiments, the vehicle consists essentially of the silicone vehicle, such as silicone oil, which can (but does not have to) comprise up to 90, 99 or even 99.9% of the composition. In other embodiments the preparation also contains materials such as other vitamins, cosmetic ingredients, herbal ingredients and/or medicaments as desired. Due to the non-polar nature of the vehicle, the ascorbic acid is not solublized in the vehicle. Therefore, the preparation is best described as a suspension of ascorbic acid in the vehicle. This lack of solubility minimizes or precludes ionization of the ascorbic acid molecule, which results in a significant enhancement in the stability of this biologically active substance. Furthermore, the use of a silicone based non-aqueous vehicle in which to deliver high levels of ascorbic acid to the skin does not require the presence of additional ingredients such as metal chelators [for example ethylenediamine tetraacetic acid (EDTA), diethylene triaminepentaacetic acid (DTPA) or ethylenediamine di-(o-hydroxyphenylacetic acid) (EDDHA)] in order to enhance the stability of ascorbic acid against oxidation by trace quantities of metal ions in the water, and other ingredients commonly used in topical preparations.

Of particular interest, it has been discovered that silicone gels or solids are the preferred silicone-based vehicles from which to formulate the non-aqueous, preferably anhydrous (less than 0. 1 % water) vehicle. The exact reasons for the superiority of silicone oils are unknown, but is believed to be the result of the ability of such oils to substantially preclude absorption of water or oxygen. The substantial absence of water or oxygen absorption by the non-aqueous vehicle can minimize or eliminate the most common sources of instability of ascorbic acid without the need for expensive chemical modifications of the molecule. Therefore, the present invention permits economical preparations of ascorbic acid even at high levels (greater than 1% w/w ascorbic acid). Stable topical preparations can be formulated even at levels of up to 40% (w/w) ascorbic acid (or more) using this technology. The only factor limiting the maximum quantity of ascorbic acid that can be included in this preparation is the amount of the non-aqueous medium needed to thoroughly disperse the quantity of ascorbic acid desired.

Additionally, although many individuals can easily tolerate the topical application of ascorbic acid, there may be some transitory stinging upon application during the first few days of use of such a product. Therefore, such compositions may include one or more anti-irritants in order to reduce this stinging potential. Furthermore, the incorporation of such a material into the composition may, at least in some cases, allow the composition to be more readily tolerated even by those individuals who could not otherwise apply an ascorbic acid preparation to their skin because of irritation and/or persistent stinging.

In disclosed embodiments, the topical composition comprises a particulate ascorbic acid, and a silicone vehicle (such as an oil, gel or solid) in a sufficient amount to suspend (substantially without solubilizing) an effective amount of the particulate ascorbic acid, and substantially excluding environmental oxygen and moisture from the composition. The particulate ascorbic acid consists essentially of solid ascorbic acid particles having a particle size of less than about 20 $\mu$m, for example less than about 12 $\mu$m. The silicone vehicle comprises at least 50% by weight of the composition, for example at least 80% by weight of the composition, and even up to 99% or 99.9% of the composition.

In particular embodiments, the silicone oil is an organosiloxane, such as one or more of a polyorganosiloxane selected from the group consisting of polysilicone-11, dimethicone and cyclomethicone. The particulate ascorbic acid is present in an amount of at least 0. 1% of undissolved ascorbic acid, for example at least 1% of undissolved ascorbic acid, for example 2 to 30%, 5 to 20%, 8 to 12%, or even as much as 40% or more of ascorbic acid. The silicone oil substantially excludes moisture, and the ascorbic acid is substantially insoluble in the silicone oil, hence the composition is substantially free of dissolved ascorbic acid or water. The composition may optionally include Vitamin E or Vitamin A, where the Vitamin E may be in the form of tocopherol or its esters (for example tocopheryl acetate), and Vitamin A may be in the form of retinol or its ester or acids (for example retinyl palmitate or retinoic acid).

In other embodiments, the composition includes an anhydrous silicone carrier, in an amount of 50–80% by weight, which is substantially free of water or environmental (for example atmospheric) oxygen, and particulate ascorbic acid, in an amount of 0.1–40% by weight, having a particle size of less than about 12.5 $\mu$m, and which is stable to oxidation of ascorbic acid by environmental oxygen. The composition may comprise one of more of Vitamin A and Vitamin E, and other ingredients to be delivered to the skin, such as herbal ingredients and medicaments, or materials designed to reduce stinging or irritation of the skin to which the composition is applied. The silicone oil vehicle may include dimethicone, cyclomethicone, polysilicone-11, or mixtures of these and other organosiloxane materials in any given ratio in order to achieve the desired consistency and application characteristics depending upon the intended application (e.g., to a particular area such as the skin, hair, or eyes).

The foregoing and other objects, features, and advantages of the invention will become more apparent from the following detailed description of particular embodiments. cl DETAILED DESCRIPTION OF SOME PARTICULAR EMBODIMENTS The stabilized ascorbic acid suspension of the present invention includes a silicone vehicle (such as an oil, gel or solid) that is ideally substantially anhydrous (e.g. less than 0.1% water), supports a suspension of ascorbic acid, and is not hygroscopic so that it does not absorb sufficient water from the atmosphere to initiate the decomposition of ascorbic acid in the suspension. Particular embodiments of the vehicle also substantially exclude metal ions (such as zinc ions) or other materials (such as organic chemical ingredients with double bonds) that would react with or oxidize the ascorbic acid. The vehicle is also substantially non-polar, and does not have significant solvating power for ascorbic acid (as do polar organic solvents such as alcohols).

Gel or solid forms of the silicone vehicle are particularly preferred because they maintain a more uniform suspension (and dosage) of the ascorbic acid in the product throughout its shelf life. However emulsifiers would not be suitable solvents, because an emulsifier must have some water solubility in order to stabilize the interface between the oil and water phases. For example, silicone copolyol emulsifiers would have some water solubility, and also absorb water from the atmosphere (via its polyol functionality).

The silicone vehicle may be a volatile or non-volatile silicone. In some disclosed embodiments the formulation incorporates volatile silicone oils (such as cyclomethicone) to achieve a consistency that is aesthetically pleasing when applied to the face. However, in other formulations (such as pharmaceutical formulations, or products to be applied to the body instead of the face), other than volatile silicone oils may be used.

The following examples are included for purposes of illustrating the technology covered by this disclosure. They are not intended to limit the scope of the claimed invention in any manner. One skilled in the art will understand that there are alternatives to these specific embodiments that are not completely described by these examples.

EXAMPLES 1–4

Preparations containing 10 (w/w) % ascorbic acid, with and without an ester of Vitamin E (tocopheryl acetate), are shown in Table 1. All amounts in this specification are percentages by weight (w/w) unless otherwise noted.

TABLE 1

| Ingredients | Example 1 | Example 2 | Example 3 | Example 4 |
|---|---|---|---|---|
| Polysilicone-11 | 0.1–68.0 | 34.0 | 34.0 | 34.0 |
| Dimethicone | 0.1–36.0 | 23.0 | 20.5 | 20.5 |
| Cycolmethicone | 0.1–56.0 | 33.0 | 30.5 | 30.5 |
| Ascorbic Acid | 0.1–30.0 | 10.0 | 10.0 | 10.0 |
| Tocopheryl Acetate | 0.0–10.0 | — | 5.0 | 5.0 |
| Retinyl Palmitate | 0.0–5.0 | — | — | 0.005 |
| Total | 100 | 100 | 100 | 100 |

Polysilicone-11 is a cross-linked silicone rubber formed by the reaction of vinyl-terminated silicone and methylhydrodimethyl siloxane in the presence of cyclomethicone. The ingredients listed in Table 1 can be obtained from the suppliers shown in Table 2:

TABLE 2

| Ingredient and Trade Name | Supplier | Address |
|---|---|---|
| Dimethicone and Polysilicone-11 (Gransil DMG-6) | Grant Industries, Inc. | Grant Industries, Inc. Elmwood, NJ 07407 |
| Cyclomethicone and Polysilicone-11 (Gransil GCM-5) | Grant Industries, Inc. | Grant Industries, Inc. Elmwood, NJ 07407 |
| Tocopheryl Acetate (Vitamin E Acetate) | Roche Vitamins and Fine Chemicals | Hoffmann-La Roche Nutley, NJ 07110-1199 |
| Retinyl Acetate (Vitamin A Acetate) | Roche Vitamins and Fine Chemicals | Hoffmann-La Roche Nutley, NJ 07110-1199 |

Method of Making: Combine the Polysilicone-11, dimethicone and cyclomethicone in a container. The tocopheryl acetate and retinyl palmitate are added as appropriate and mixed until uniform. The solids (ascorbic acid) are dispersed into this mixture with appropriate agitation. The ascorbic acid is ground into the mixture using a three-roll mill until the particle size of the solid ascorbic acid particles is small enough that the particles are not gritty when applied to the skin (particle size less than 12.5 microns as measured by a Hagman gauge). Mix until uniform, then package the resulting white to off-white formulation in containers.

As an alternative procedure, Ultrafine ascorbic acid can be use to replace the granular ascorbic acid. Using this material eliminates the need to pass the batch through a device to reduce the particle size. Roche Vitamins and Fine Chemicals lists the following specification for this material, which is sold under the name ascorbic acid USP, FCC (Vitamin C; L-ascorbic acid) Ultra-Fine Powder (Product Code No. 6045653), in which 100% of the powder passes through a No. 100 U.S. Standard Sieve (a standard USP and FCC testing procedure). Alternatively, more than 80% of the material passes through a No. 325 U.S. Sieve.

The product made by Example 4 is a white to off-white cream-gel having no appreciable odor, a viscosity of 30,000 to 150,000 CPS, and a specific gravity of 0.97–1.03.

EXAMPLE 5

The product made in Example 4 was stored under conditions of elevated temperature and humidity in order to check for the stability of the ascorbic acid. Ascorbic acid stability was determined by the absence of an off-white to brown coloration characteristic of degraded ascorbic acid. The product used was manufactured under laboratory conditions and packaged without special precautions to exclude air or oxygen from contacting the product (i.e., without blanketing the resulting product with nitrogen to reduce the potential of oxidation by air or oxygen). The results of this stability study are shown in Table 3.

TABLE 3

Coloration of Samples Stored at Varying Conditions

| Duration of Storage | Storage Conditions | | |
|---|---|---|---|
| | Room Temperature | 40° C./80% R.H. | 50° C./Ambient R.H. |
| 1 Week | White | White | White |
| 2 Weeks | White | White | White |
| 3 Weeks | White | White | White |
| 1 Month | White | White | White |
| 2 Months | White | — | — |
| 3 Months | White | — | — |
| 6 Months | White | — | — |
| 9 Months | WHite | — | — |

According to guidelines used by the U.S. Food and Drug Administration, the stability of the samples stored at 40° C./80% relative humidity are indicative of a formulation that is stable for a period of time equivalent to 8 times its stable storage period. Therefore, the data in Table 3 confirms that the ascorbic acid formulation of the present invention will remain stable for at least 8 months at ambient temperature. In particular embodiments, it is preferred that the formulation in Example 4 containing 10 (w/w) % ascorbic acid will remain stable for at least 2 years without the need for any special handling procedures during the manufacturing and packaging processes, or during handling by the consumer.

EXAMPLE 6

A product made in accordance with Example 4 was tested for antioxidant activity in human skin cell cultures using ultraviolet light from a solar simulator as the source of free radicals within the skin cells.

Antioxidant activity was evaluated in cell culture using the Epiderm Skin Model (EPI-100) from the Mattek Corporation of Ashland, Mass. These cell cultures of neonatal foreskin were cultured in accordance with the manufacturer s directions, and were assayed for percent cellular viability by measuring the amount of 3-(4,5-dimethylthazol-2-yl)-2, 5-diphenyltetrazolium bromide (MTT) dye taken up by the cell cultures. Viable cells take up this dye and convert it to insoluble formazin crystals that resides in the mitochondria of the cells until extracted with alcohol. The amount of MTT converted to extractable formazin crystals is directly proportional to the viability of the cell culture. MTT is measured spectrophotometrically. Cells exposed to UV light at a rate of 1.5 Minimal Erythemal Dose (MED) per hour per square centimeter from a solar simulator (filtered to yield wavelengths in the region of 290–400 nm) in the presence of the ascorbic acid composition or mixtures were used to measure the effect of antioxidants to protect the cell culture from the generation of free radicals. The total dose of ultraviolet light was 31.5 mJ/cm$^2$.

The cell cultures were also evaluated for the production of Prostaglandin $E_2$ (PGE$_2$) using an assay kit obtained from PerSpective Diagnostics of Cambridge, Mass. As with the assay for percent cellular viability, the cell cultures were exposed to a dose of ultraviolet light at a rate of 1.5 MED per hour per square centimeter from a solar simulator in the presence of the ascorbic acid compositions or controls. The total dose of ultraviolet light was 31.5 mJ/cm². These cell cultures were then allowed to stand in normal growth media for 24 hours. After being allowed to grow for that period of time, the cell cultures were assayed for production of $PGE_2$ using the assay kit from PerSpective Diagnostics.

Exposure of the skin to ultraviolet (UV) light is known to generate free radicals in skin cells. The endpoints used to measure the antioxidant activity were the (1) the number of viable cells remaining after exposure to the UV light as determined by the conversion of 3-(4,5-dimethylthazol-2-yl)-2,5-diphenyltetralium bromide (MTT) to extractable formazin crystals by the viable cells; and (2) the amount of Prostaglandin $E_2$ ($PGE_2$) produced by the cells in response to the exposure to the UV light. The data from these endpoints were compared to a negative control (cell cultures exposed to UV light without the presence of any antioxidants) and a positive control (cell cultures not exposed to UV light). An effective product is one that has more viable cells than the negative control, and produces less Prostaglandin E2 than the negative control. The results of these tests are shown in Table 4.

TABLE 4

Results of Antioxidant Testing on Example 4 and Negative Control

| Test | Example 4 | Negative Control |
|---|---|---|
| Percent Viable Cells Remaining | 75.8 | 5.8 |
| Prostaglandin Produced (ng/ml) | 11,200 | 17,500 |

These results clearly indicate that the ascorbic acid formulation exhibits antioxidant activity.

EXAMPLE 7

The formulation of Example 4 was also subjected to a clinical test on human subjects in which the skin was subjectively and objectively measured for product efficacy. Each of 20 subjects in the test applied the formulation in Example 4 to one side of the face twice daily for a period of 3 months. The side of the face to which the formulation was applied was randomly assigned by the study investigator to eliminate any bias. Subjects were subjectively evaluated for irritation and objectively measured for changes in elasticity and texture. Elasticity changes were evaluated by the use of a CUTOMETER™, which measures the ability to elastically deform the skin under a vacuum. Changes in fine lines and wrinkles were evaluated by image analysis of skin replicas taken on the treated and untreated site at each visit. The results of these evaluations are shown in Table 5.

TABLE 5

Results of Clinical Evaluations

| Change in Appearance | Percentage Change[a] | Measurement Timeframe[b] |
|---|---|---|
| Reduction of Fine Lines | 11% | 2 weeks |
| Reduction of Wrinkles | 14% | 4 weeks |
| Increase in Elasticity | 42% | 2 weeks |

[a]Percentage Improvement is calculated from the following equation: [(Treated - Untreated)/Untreated] × (100).
[b]The length of time between the start of product use and the measurement.

The data in Table 5 clearly indicates that the product is effective at improving skin elasticity and the appearance of fine lines and wrinkles. This data is interpreted as representing a dramatic improvement in the amounts of collagen in the skin that results in an increased skin elasticity and a simultaneous improvement in skin texture (i.e. a reduction in fine lines and wrinkles). Since the skin's moisture levels were not significantly enhanced (data not shown), these changes must be the result of the increased collagen production.

As used in this specification, the term "silicone" refers to organosiloxanes or polyorganosiloxanes, which are any of a large group of siloxane polymers based on a structure in which silicon and oxygen atoms alternate with various organic radicals attached to the silicon, as described for example in Remington: The Science and Practice of Pharmacy, 19th edition, pages 867–868, and as shown below:

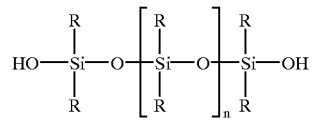

The organosiloxanes may be liquids, semisolids, or solids depending on the molecular weight and degree of polymerization, as known in the art. A silicone oil is the preferred vehicle. A "silicone oil" is a liquid organosiloxane.

A "suspension" is a system in which small particles (such as ascorbic acid particles) are substantially uniformly dispersed in a liquid, gel, or cream medium. An emulsion is specifically excluded from the definition of a suspension. A solid may be formed from the suspension.

A "volatile silicone oil" is a silicone oil have a low heat of vaporization, i.e. normally less than about 50 cal per gram of silicone oil. Typical suitable volatile silicone oils include cyclomethicones such as Dow Corning 344 Fluid, Dow Corning 345 Fluid, Dow Corning 244 Fluid, and Dow Corning 245 Fluid; as well as Volatile Silicon 7207, a trademark of Union Carbide Corp., Danbury, Conn., low viscosity dimethicones, i.e. dimethicones having a viscosity of about 50 cst or less, especially dimethicones such as Dow Corning 200-0.5 cst Fluid. The Dow Corning Fluids are available from Dow Corning Corporation, Midland, Mich. 48640. Cyclomethicone and dimethicone are names given by the Third Edition of the CTFA Cosmetic Ingredient Dictionary to cyclic dimethyl polysiloxane compounds and a mixture of fully methylated linear siloxane polymers end-blocked with trimethylsiloxy units, respectively. Other volatile silicone oils having a low heat of vaporization, such as those available from General Electric Co., Silicone Products Div., Waterford, N.Y. and SWS Silicones Div. of Stauffer Chemical Co., Adrian, Mich., can also be used in the compositions of the invention.

With reference to the ascorbic acid compositions described herein, the term "effective amount of ascorbic acid" means an amount sufficient to reduce fine lines and wrinkles in the skin, or to increase elasticity, or both. In the disclosed embodiments of this invention, that effective amount can be at least about 0.1% of ascorbic acid, for example about 0.1–30%, or at least about 1%, 10%, or even 40% of ascorbic acid.

An "effective amount" of Vitamin A, Vitamin C, or Vitamin E is an amount sufficient to have an antioxidant effect, as measured by the methods of Example 6, that is an increase in cellular viability or a reduction in the production of $PGE_2$.

An "effective amount" of silicone oil is an amount sufficient to substantially exclude environmental (for example atmospheric) water or oxygen. A "nonaqueous" composition is one that is substantially water free. While water is not intentionally added to a nonaqueous composition, no attempt is made to remove water from the ingredients used in the compositions, since it is not necessary that the compositions be completely anhydrous. However, it is desired that the amount of free water in the composition be less than about 1%, or even less than 0.1% (at which point is would be considered substantially anhydrous).

A "topical" composition is one that is suitable for application to the skin, and includes pharmaceutical and cosmetic formulations. A pharmaceutical composition is one that is intended to deliver therapeutic substances, and can include conventional preparations for administration on the skin (topical or dermatologic), or in the eye (ophthalmic), among others.

The nonaqueous ascorbic acid compositions of the invention can contain conventional amounts of one or more cosmetic waxes, cosmetic emollients, and even sunscreening agents. The compositions may also contain perfumes, preservatives, dyes, softeners, physical reflectors and antioxidants, as well as any other class of materials whose presence may be cosmetically or otherwise desirable.

Cosmetic antioxidants include propyl, octyl and dodecyl esters of gallic acid, butylated hydroxyanisole (usually as a mixture of ortho and meta isomers), butylated hydroxytoluene and nordihydroguaiaretic acid. Although such antioxidants have been added to ascorbic acid compositions in the past, it is unnecessary to add antioxidants to the ascorbic acid compositions of the present invention, because the silicone vehicle substantially excludes atmospheric water and oxygen from the composition. However, the present invention can also include compositions to which such preservatives are added.

The compositions of the present invention may be in the form of a liquid, gel or semi-solid. The selection of ingredient type and amount is dictated by the nature of the composition, i.e. gel or semi-solid, and is within the skill of cosmetic chemists. Thus larger amounts of wax may be incorporated into the semi-solid compositions of the present invention than into the liquid ones.

Typical suitable cosmetic waxes include ozokerite, lanolin alcohol, paraffin wax, bayberry wax, polyethylene wax, especially AC 617 available from Allied-Signal Corp., Morristown, N.J.; Polawax (a reaction product of higher fatty alcohols and ethylene oxide available from Croda, Inc., New York., N.Y. 10016), trihydroxystearin, lanolin wax, beeswax, Candellila wax, microcrystalline wax, Carnauba wax, cetyl alcohol, stearyl alcohol, spermaceti, cocoa butter, fatty acids of lanolin, mono-, di- and tri-behenate (a triester of behenic acid and glycerine) and $C_{18}$–$C_{36}$ acid triglyceride (a mixture of triesters of $C_{18}$–$C_{36}$ carboxylic acids and glycerine), available from Croda, Inc., New York, N.Y., under the tradenames Syncrowax HRC and Syncrowax HGL-C, respectively, fatty esters which are solid at 25° C., silicone waxes such as methyloctadecaneoxypolysiloxane and poly (dimethylsiloxy) stearoxysiloxane, stearyl mono- and diethanolamide, rosin and its derivatives such as the abietates of glycol and glycerol, hydrogenated oils solid at 25° C., and sucroglycerides.

Typical suitable cosmetic emollients include mineral oil, especially mineral oils having a viscosity in the range of 50 to 500 SUS, lanolin oil, coconut oil, cocoa butter, olive oil, almond oil, macadamia nut oil, aloe extract, jojoba oil, safflower oil, corn oil, liquid lanolin, cottonseed oil, and peanut oil. Other typical suitable cosmetic emollients include Purcellin oil, perhydrosqualene, castor oil, polybutene, odorless mineral spirits, sweet almond oil, avocado oil, calophyllum oil, ricin oil, vitamin E acetate, olive oil, mineral spirits, linolenic alcohol, oleyl alcohol, the oil of cereal germs, such as the oil of wheat germ, and esters such as isopropyl myristate, butyl myristate, hexadecyl stearate, decyl oleate, acetyl glycerides, the octanoates and benzoates of(C12–C15) alcohols, the octanoates and decanoates of alcohols and polyalcohols such as those of glycol and glycerol, ricin oleates of alcohols and poly alcohols, such as those of isopropyl adipate, hexyl laurate and octyl dodecanoate.

Other suitable cosmetic emollients which are solids or semi-solids at ambient temperatures may be used if admixed with one or more of the cosmetic emollients listed above, in amounts sufficient to provide liquid topical compositions. Such solid or semi-solid cosmetic emollients included hydrogenated lanolin, hydroxylated lanolin, acetylated lanolin, petrolatum, isopropyl lanolate, cetyl myristate, myristyl myristate, myristyl lactate, cetyl alcohol, isostearyl alcohol and isocetyl lanolate.

The ascorbic acid composition can also include other ingredients to be delivered to the skin, such as herbal ingredients and medicaments. Examples of such herbal ingredients and medicaments are shown in the following Tables 6 and 7:

TABLE 6

Herbal Ingredients

| Name | Description | Formulation Concentration Range | Anticipated Delivery Concentration Range to the skin |
| --- | --- | --- | --- |
| Saxifraga Stolonifera Extract, Grape Extract, Mulberry Root Extract, and Scutellaria Root Extract | A combination of ingredients reported to aid in producing a more even skin tone | 0.01 to 5% | 10–20% of the applied dose |
| Fagus Salvitical Extract | A material that is reported to gently increase cell turnover rates | 0.01 to 10% | 10–20% of the applied dose |
| Green Tea Extract | A material that is reported to soothe the skin and that exhibits antioxidant properties | 0.01 to 20% | 10–20% of the applied dose |
| Billbery Extract | A material that is reported to soothe the skin and that exhibits antioxidant | 0.01 to 20% | 10–20% of the applied dose |

TABLE 6-continued

Herbal Ingredients

| Name | Description | Formulation Concentration Range | Anticipated Delivery Concentration Range to the skin |
|---|---|---|---|
| Chamomile Extract | properties A material that is reported to soothe the skin | 0.01 to 25% | 10–20% of the applied dose |
| Ginseng Extract | A material that is reported to soothe the skin | 0.01 to 25% | 10–20% of the applied dose |
| Licorice Extract | A material that is reported to soothe the skin | 0.01 to 25% | 10–20% of the applied dose |
| Kojic Extract | A material that is reported to aid in the production of a more even skin tone | 0.01 to 5% | 10–20% of the applied dose |
| Fruit Acid Extracts | A broad class of materials reported to enhance cell turnover rates | 0.01 to 30% | 10–80% of the applied dose |

TABLE 7

Medicaments

| Name | Purpose | Formulation Concentration Range | Anticipated Delivery Concentration Range to the skin |
|---|---|---|---|
| Hydroquinone | Skin bleaching agent | 0.01–20% | 10–80% of the applied dose |
| Sulfur, resorcinol, salicylic acid, tretinoin and/or antibiotics | Treatment of acne | 0.01–20% | 10–80% of the applied dose |
| Antibiotics (Bacitracin, Neomycin, Polymixin B Sulfate), Antifungals (Undecylenic Acid, Miconazole, Tolnaftate), Antiseptics (iodine, chlorhexidine gluconate, thimerosal), Phenolic (phenol, Triclosan, thymol) | Treatment of topical infections | 0.01–20% | 10–80% of the applied dose |
| Skin Protectants (allantoin, calamine, shark liver oil, tannic acid) | Treatment of dry skin | 0.01–20% | 10–80% of the applied dose |
| Materials such as urea, lactic acid, allantoin and hydrocortisone | Treatment of dermatitis | 0.01–40% | 10–80% of the applied dose |
| Materials such as coal tar, salicylic acid, sulfur and zinc pyrithione | Treatment of dandruff, seborrhea, psoriasis | 0.01–20% | 10–80% of the applied dose |

The composition can also include additional silicone-based materials, such as phenyl trimethicone or trimethylsilylamodimethicone, in order to achieve the desired application characteristic needed for application of the ascorbic acid to any intended body site (i.e., skin, hair, eyes, etc.). Examples 8 to 11 show such alternative formulations.

Example 8
Hair Gloss

| Phenyl Trimethicone | 5–20% |
|---|---|
| Cyclomethicone | 40–94.9% |
| Ascorbic Acid | 0.1–40% |
| Fragrance | q.s. |
| Total | 100% |

Example 9
Hair Conditioner

| Cyclomethicone | 10–40% |
|---|---|
| Dimethicone | 20–50% |
| Phenyl Trimethicone | 15–45 % |
| Ascorbic Acid | 0.1–40% |
| Isohexadecane | 1–20% |
| Fragrance | q.s. |
| Total | 100% |

Example 10
Hair Conditioner

| | |
|---|---|
| Cyclomethicone | 45–99% |
| Trimethylsilylamodimethicone | 0.5–5% |
| Ascorbic Acid | 0.1–40% |
| Total | 100% |

Example 11
Ophthalmic Preparation

| | |
|---|---|
| Dimethicone | 40–99.9% |
| Cyclomethicone | 0.0–50% |
| Stearoxytrimethylsilane | 0.0–10% |
| Domethiconol | 0.0–10% |
| Polysilicone-11 | 0.0–40% |
| Ascorbic Acid | 0.1–40% |
| Total | 100% |

The composition may also contain a material or mixture of materials that reduces the stinging and/or irritation potential of the preparation upon application, such as any one or a combination of a variety of anesthetics, antipruritics, and counterirritants. Examples of such materials (and amounts in which they would be used) are shown in the following Table 8, and are further described in the Handbook of Non-Prescription Drugs, Ninth Edition, E. G. Feldman (editor) (American Pharmaceutical Association, Washington, D.C., 1990):

TABLE 8

| Ingredient (Reference) | Type | Concentration |
|---|---|---|
| Benzocaine | Local Anesthetic | 0.1 to 50% |
| Lidocaine | Local Anesthetic | 0.05 to 40% |
| Benzyl Alcohol | Local Anesthetic | 0.1 to 50% |
| Camphor | Local Anesthetic, Counterirritant | 0.3 to 30% |
| Menthol | Local Anesthetic, Counterirritant | 0.01 to 20% |
| Hydrocortisone | Antipruritic | 0.1 to 10% |
| Methyl Nicotinate | Counterirritant | 0.05 to 2.0% |
| Methyl Salicylate | Counterirritant | 0.1 to 60% |
| Eucalyptus Oils | Counterirritant | 0.05 to 30% |

In view of the many possible embodiments to which the principles of our invention may be applied, it should be recognized that the illustrated embodiments are only examples of the invention and should not be taken as a limitation on the scope of the invention. Rather, the scope of the invention is defined by the following claims. We therefore claim as our invention all that comes within the scope and spirit of these claims.

What is claimed is:

1. A topical composition, comprising:
   particulate ascorbic acid in an amount of 0.1–40 % by weight; and
   a nonaqueous silicone carrier, in an amount of 50–99.9% by weight, wherein the nonaqueous silicone carrier is in a sufficient amount to suspend an effective amount of the particulate ascorbic acid, the particulate ascorbic acid is substantially insoluble in the silicone carrier, and the particulate ascorbic acid consists essentially of anhydrous solid ascorbic acid particles having a particle size of less than about 20 µm, wherein the composition comprises less than 10% water by weight.

2. The composition of claim 1, wherein the particulate ascorbic acid consists essentially of solid ascorbic acid particles having a particle size of less than about 12 µm.

3. The composition of claim 1, wherein the silicone is an anhydrous silicone carrier.

4. The composition of claim 3, wherein the silicone carrier is a polyorganosiloxane.

5. The composition of claim 4, wherein the polyorganosiloxane carrier is selected from the group consisting of polysilicone-11, dimethicone, phenyl trimethicone, trimethylsilylamodimethicone, stearoxytrimethylsilane, and cyclomethicone.

6. The composition of claim 1, wherein the particulate ascorbic acid is present in the range of 2 to 30% by weight.

7. The composition of claim 1, wherein the particulate ascorbic acid is present in the range of 5 to 20% by weight.

8. The composition of claim 1, wherein the particulate ascorbic acid is present in the range of 8 to 12% by weight.

9. The composition of claim 1, wherein the composition is substantially free of dissolved ascorbic acid.

10. The composition of claim 1, further comprising one or more of Vitamin A and Vitamin E.

11. The composition of claim 1, wherein the composition is substantially free of metal ions that oxidize ascorbic acid.

12. A composition comprising:
   a silicone vehicle, in an amount of 50–80% by weight, which is substantially free of water or atmospheric oxygen, and in which ascorbic acid is substantially insoluble; and
   particulate anhydrous ascorbic acid, in an amount of 0.1–40% by weight, having a particle size of less than about 12.5 µm, and which is substantially insoluble in the silicone vehicle, wherein the composition is non-aqueous and stable to oxidation of ascorbic acid by atmospheric oxygen; and the composition comprises less than 10% water by weight.

13. The composition of claim 12, further comprising one or more of Vitamin A and Vitamin E.

14. The composition of claim 13, the Vitamin E is in the form of tocopherol or its esters, and Vitamin A is in the of retinol or its ester or acids.

15. The composition of claim 14, wherein the Vitamin E is tocopheryl acetate, and the Vitamin A is retinyl palmitate or retinoic acid.

16. The composition of claim 2, further comprising other ingredients to be delivered to the skin.

17. The composition of claim 16, wherein the other ingredients comprise herbal ingredients and medicaments.

18. The composition of claim 12, wherein the silicone vehicle includes one or more of a combination of dimethicone, cyclomethicone and polysilicone-11.

19. The composition of claim 12, further comprising additional silicone-based materials to customize the composition for application to an intended body site.

20. The composition of claim 12, further comprising an ingredient that reduces the stinging and/or irritation of the composition upon application to the skin.

21. A method of improving skin appearance, comprising applying an effective amount of the composition of claim 1 to the skin.

22. The composition of claim 1, wherein the composition comprises less than 1% water by weight.

23. The composition of claim 1, wherein the composition comprises less than 0.1% water by weight.

24. The composition of claim 1, wherein the composition is anhydrous.

* * * * *

UNITED STATES PATENT AND TRADEMARK OFFICE
CERTIFICATE OF CORRECTION

PATENT NO. : 6,146,664 Page 1 of 1
DATED : November 14, 2000
INVENTOR(S) : Mukhtar Siddiqui It is certified that error appears in the above-identified patent and that said Letters Patent is hereby corrected as shown below:

Title page, Item [54] and Column 1, line 1,
Title, "STABLE TOPICAL ASCORBIC ACID COMPOSITIONS"
should read -- STABLE ASCORBIC ACID COMPOSITIONS --.

Item [56], References Cited, OTHER PUBLICATIONS, list includes the following duplicate entries: "Alberts et al., 1996; Darr et al., 1992; Gensler et al., 1996; Harry, R. G., 1973; Idson, B., 1993; Manowitz, M. and Sharpell, F., 1997; Mayer et al., 1993; Mona Industries, Inc.; Paton et al., 1995; Rieger, M.M., 1993; Rigler, N.E. and Schimmel, J., 1957; VERIS Research Summary, 1997."

Column 6,
Line 20, "WHite" should read -- White --.

Column 14,
Line 2, "by weight." should read -- by weight; and a nonaqueous silicone carrier, in an amount of 50-99.9% by weight, wherein the nonaqueous silicone carrier is in a sufficient amount to suspend an effective amount of the particulate ascorbic acid, wherein the particulate ascorbic acid is substantially insoluble in the silicone carrier; wherein the composition is substantially fee of water. --
Lines 36-37, "atmospheric oxygen; and" should read -- atmospheric oxygen; wherein the composition is substantially free of water. --

Signed and Sealed this

Third Day of December, 2002

JAMES E. ROGAN
*Director of the United States Patent and Trademark Office*